United States Patent
Sieber et al.

(10) Patent No.: US 9,345,570 B2
(45) Date of Patent: May 24, 2016

(54) WIDE-ANGLE OPTICAL UNIT FOR OPHTHALMOLOGICAL IMPLANTS

(71) Applicant: KARLSRUHER INSTITUT FUER TECHNOLOGIE, Karlsruhe (DE)

(72) Inventors: Ingo Sieber, Karlsruhe (DE); Helmut Guth, Eggenstein-Leopoldshafen (DE); Georg Bretthauer, Karlsruhe (DE); Ulrich Gengenbach, Remchingen/Singen (DE); Rudolf F. Guthoff, Rostock (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 0 days.

(21) Appl. No.: 14/415,160

(22) PCT Filed: Jul. 18, 2013

(86) PCT No.: PCT/EP2013/002139
§ 371 (c)(1),
(2) Date: Jan. 16, 2015

(87) PCT Pub. No.: WO2014/015964
PCT Pub. Date: Jan. 30, 2014

(65) Prior Publication Data
US 2015/0190224 A1    Jul. 9, 2015

(30) Foreign Application Priority Data
Jul. 23, 2012    (DE) .......................... 10 2012 106 653

(51) Int. Cl.
*A61F 2/16*    (2006.01)

(52) U.S. Cl.
CPC ............. *A61F 2/1648* (2013.01); *A61F 2/1629* (2013.01); *A61F 2/1656* (2013.01)

(58) Field of Classification Search
CPC ....... A61F 2/16; A61F 2/1624; A61F 2/1635; A61F 2/1613; A61F 2/1627; A61F 2/1648; A61F 2/1651; A61F 2/1656
USPC ................................................ 623/6.22, 6.26
See application file for complete search history.

(56) References Cited

U.S. PATENT DOCUMENTS

| 5,697,973 A * | 12/1997 | Peyman ..................... A61F 2/16 623/6.26 |
| 6,358,280 B1 | 3/2002 | Herrick |
| 2006/0229720 A1 * | 10/2006 | Glazier ................. A61F 2/1613 623/6.26 |

(Continued)

FOREIGN PATENT DOCUMENTS

| DE | 19501444 A1 | 7/1996 |
| EP | 2196172 A1 | 6/2010 |

(Continued)

*Primary Examiner* — David H Willse
*Assistant Examiner* — Tiffany Shipmon
(74) *Attorney, Agent, or Firm* — Leydig, Voit & Mayer, Ltd.

(57) ABSTRACT

A wide-angle optical unit for ophthalmological implants in the eye includes a lens system arranged in a rotationally symmetrical manner about an optical axis and further includes at least two lenses that rest one on top of the other in a planar manner and which are made of materials having different optical refractive indices. In addition, the wide-angle optical unit includes an optical decoupling structure and a trailing lens arranged proximally with respect to the interior of the eye. The trailing lens is mounted around the optical decoupling structure.

12 Claims, 4 Drawing Sheets

(56) References Cited

U.S. PATENT DOCUMENTS

2009/0105817 A1     4/2009   Bretthauer et al.
2010/0145445 A1*   6/2010   Aharoni ................ A61F 2/1613
                                                             623/6.17

FOREIGN PATENT DOCUMENTS

WO        WO 0038593   A1    7/2000
WO        WO 2007020184   A1    2/2007

* cited by examiner

Fig.2a
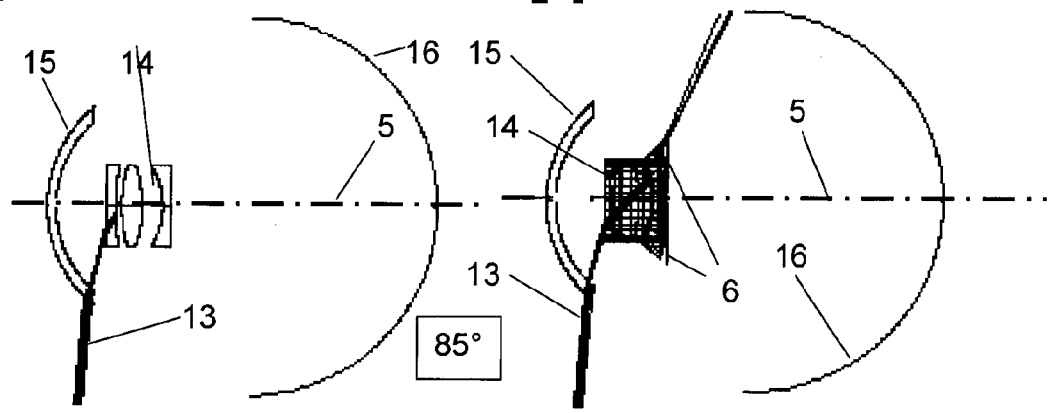
Fig.2j
85°
Fig.2b
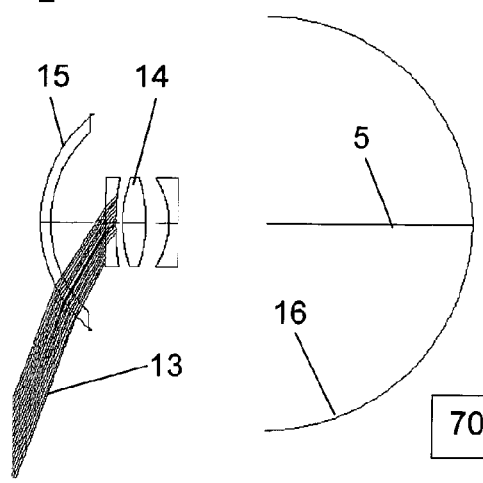
Fig.2k
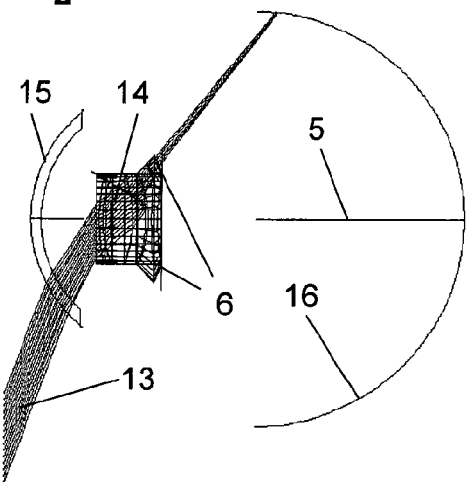
70°
Fig.2c
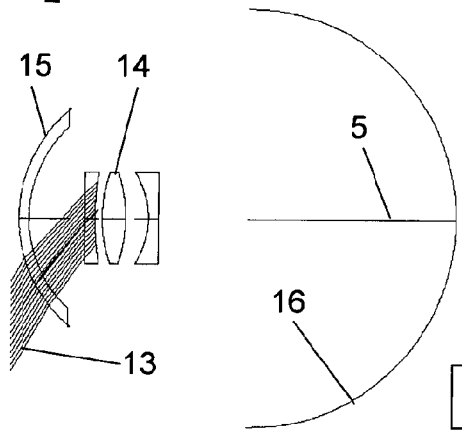
Fig.2l
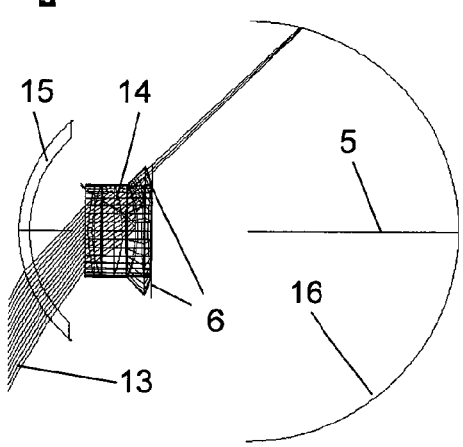
60°

50°

40°

30°

20°

10°

0°

WIDE-ANGLE OPTICAL UNIT FOR OPHTHALMOLOGICAL IMPLANTS

CROSS-REFERENCE TO RELATED APPLICATIONS

This application is a U.S. National Phase application under 35 U.S.C. §371 of International Application No. PCT/EP2013/002139 (WO 2014/015964 A1), filed on Jul. 18, 2013, and claims benefit to German Patent Application No. DE 10 2012 106 653.1, filed Jul. 23, 2012.

FIELD

The invention relates to optical units and optical systems, and in particular, to wide angle optical units and to wide-angle optical systems including such wide angle optical units for ophthalmological implants.

BACKGROUND

In ophthalmology, ophthalmological implants are used for restoring and maintaining sight. Examples of simple implants are artificial eye lenses, which replace the endogenous eye lens, by means of exchange, for example when said endogenous eye lens opacifies in the event of a grey cataract. Lenses of this type comprise one single lens. Bifocal or multifocal lenses having two or more fixed focal lengths installed in parallel are also known in ophthalmology, whereby, following a training phase and according to requirements, the patient concentrates on one of the focal widths, which are always available, according to the situation in order to favour sharper images. Typically, artificial eye lenses are a single piece, i.e. they are not lens systems comprising a plurality of lenses.

In particular recently, adjustable lens systems have also become known, in which either individual lenses which are adjustable in shape or adjustable lens systems are used.

For example, WO 2007/020184 A1 discloses an artificial system for restoring the accommodative ability. Said system comprises an optical system which is adjustable independently of the ciliary muscle and which is an actively optical element having a variable curvature, a refractive boundary surface or a variable refractive index distribution, or is a shiftable, passive optical element having unchanging optical properties, or is the combination of one or more active and/or passive optical elements.

WO 2000/38593 A1 also discloses an eye implant which comprises a plurality of lenses in a substantially cylindrical housing and is inserted into the eye by means of haptic elements. The implant is distinguished not only on account of its preferably cylindrical design centred about an optical axis, but also in that the cylindrical outer surface is impermeable to light.

Owing to their geometric and optical basic parameters, such as the miniaturisation required as a result of the dimensions in the eye, most complex optical systems, such as that described above, which are implanted in the eye in place of or in addition to the human lens, greatly restrict the field of vision of the potential patient. The described eye implants thus differ fundamentally from the optical units known in optical measuring technology and/or from the field of lenses. The natural human eye has a vertical field of vision of approximately 130° and a horizontal field of vision of approximately 180°. This means in particular that the peripheral vision of the patient in the vertical and horizontal directions is severely impaired when a complex structure is implanted. With an artificial accommodation system, for example as proposed in WO 2007/020184 A1, a restricted field of vision of at most 80° has to be expected, which leads to what is referred to as tunnel vision. Peripheral vision, however, is essential for a person to orient themselves in space, for orientation in twilight and darkness, and for the ability of said person to react to lateral stimuli.

Conventional wide-angle systems and optical systems containing said wide-angle systems on their own are not suitable for use in the human eye, since the idea behind them is to project the wide-angle range in the object plane onto a defined, small region in the image plane (film, camera chip).

SUMMARY

In an embodiment, the present invention provides a wide-angle optical unit for ophthalmological implants in the eye, the wide-angle optical unit including a lens system arranged in a rotationally symmetrical manner about an optical axis, the lens system including at least two lenses that rest one on top of the other in a planar manner and that are made of materials having different optical refractive indices, an optical decoupling structure, and a trailing lens arranged proximally with respect to the interior of the eye and mounted around the optical decoupling structure.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
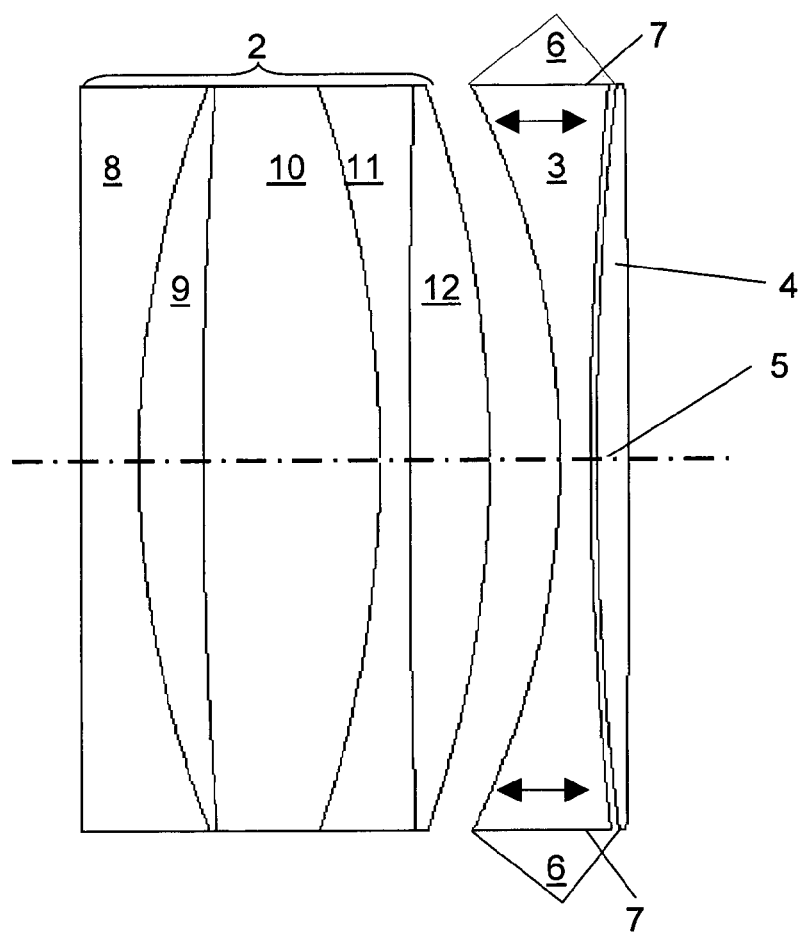
FIG. 1 is a section through an embodiment of the optical system comprising a wide-angle optical unit and a shifting lens.

The wide-angle optical unit is a component of a preferably ophthalmological implant for restoring the accommodative ability. Said unit comprises an optical unit having a high angular acceptance, and a decoupling structure. Said unit does not necessarily comprise the optical adjustment mechanism of the accommodation system. Together with the optical adjustment mechanism and optionally separate emergent surfaces or emergent components, the wide-angle optical unit forms an optical system.

An embodiment of the invention provides a wide-angle optical unit for ophthalmological implants in the eye, which, owing to their design and structure, restrict the field of vision of the patient, such that said optical unit does not restrict sight in a central field of view and at the same time ensures the implant wearer has peripheral vision.

A wide-angle optical unit of an optical system for ophthalmological implants in the eye is provided herein according to one embodiment of the invention, which unit comprises at least one lens system which is arranged in a rotationally symmetrical manner about an optical axis and has at least two lenses which preferably rest on one another in a planar manner and are made of different materials, a system oriented according to the optical axis for setting the refractive power, and a decoupling structure.

The optical system comprises a distal side, i.e. a side facing away from the retina, and a proximal side facing the retina, which are each formed by a distal and a proximal optical emergent surface. Preferably, the lens system of the wide-angle optical unit is arranged on the distal side, and the decoupling structure is arranged on the proximal side in the optical system. Preferably, a first lens of the lens system forms the distal emergent surface and coupling surface to the anterior eye chamber of the eye filled with aqueous humour. The proximal emergent surface of the optical system directly adjoins the vitreous body and is preferably formed by an exit window. The exit window is optionally designed as an optical lens, the trailing lens, and as such forms the proximal end lens of the lens system towards the vitreous body of the eye. The exit window is preferably an integral component of a housing of the optical system.

The light ray is refracted at the boundary surfaces between two portions, in each case, having different refractive indices. A light ray that is incident on the eye is thus first refracted at the outer surface of the curved cornea of the eye, then refracted between the inner face of the cornea and the aqueous humour in the anterior eye chamber, and subsequently from there into the transition regions into the distal emergent surface of the distal lens of the lens system.

One feature relates to the lens system, in particular in the region of the distal emergent surface. Said system is designed such that a light ray that is incident through the distal emergent surface is refracted by the emergent surface in order to also detect the peripheral visual range even at relatively large incident angles in the range between 80 and 90° or 80 and 95°, preferably between 80 and 85°, and is passed on in the lens system at the transitions between two lenses, without total reflection. Preferably, the emergent surface is flat, the light ray impinging on the eye at an incident angle of 90° being aligned in parallel therewith, yet impinging on regions of the natural spherical cornea surface and also being refracted in this region. The aforementioned first light refractions in the region of the cornea alone make the lens system suitable for picking up incident angles of from more than 80° to more than 90°, even with a flat emergent surface.

For this purpose, the lenses of the lens system comprise different refractive indices, the refractive index of each lens of the lens system varying in steps, preferably in an alternating manner, with respect to each adjacent lens starting from the distal emergent surface.

The optical unit of variable refractive power of the optical system consists of mechanically shiftable lens combinations (e.g. shifting lens) and/or lens bodies of adjustable focal length, preferably in a volume filled with an inert gas.

The boundary surfaces between the gas and an optical element (lens, exit window or any other optical fixed body) each represent a significant change in the refractive index which is required for setting the focal length of the optical system. The optical unit of high angular acceptance is formed by successive lenses having preferably alternating refractive indices, such that the beams impinging on the optical boundary surfaces are below the critical angle of total reflection.

Another feature of the wide-angle optical unit is a decoupling structure which, as a separate optical component, deflects the passed-on light rays, in particular from incident angles of from more than 40° to more than 90°, to peripheral regions of the retina.

Embodiments of the invention may additionally comprise an annular peripheral boundary surface on the lens which forms the proximal end of the optical system, onto which boundary surface an annular optical decoupling structure is mounted and which preferably has an optical quality. The decoupling structure is preferably formed as an annular prism and as such is preferably arranged about the proximal optical unit, the refractive index of which can be set in a variable manner (e.g. shifting lens). In the context of the invention, in addition to a closed annular element having a constant or varying structure cross section or prism cross section, the terms decoupling structure and annular prism also include annular segments (partial annular prisms) which only cover certain boundary surface portions instead of the entire peripheral boundary surface. For example, a decoupling structure, annular prism or a plurality of different annular segments having different structure cross sections or prism cross sections can be arranged on the boundary surface and allow, for example, a field of view of 180° in the horizontal direction and of only 130° in the vertical direction.

The decoupling structure is used to increase the wide-angle acceptance of ophthalmological implants, which, owing to their design or structure, restrict the field of vision of the patient, and to transfer the wide-angle acceptance into the range of the natural human eye and to thus ensure or expand the peripheral vision of the implant wearer.

The image range which can be detected by the eye is divided by the decoupling structure into a central region of relatively high resolution and a peripheral edge region of relatively low resolution, and is thus adapted to the optical resolving power of the retina. The natural human eye has a vertical field of vision (field of view) of approximately 130° and a horizontal field of vision of approximately 180°, i.e. approximately ±65° vertically and approximately ±90° horizontally about the line of symmetry of the eye lenses or the eye orientation.

In the absence of additional measures, tunnel vision restricts the field of view of a fitted ophthalmological implant, since in particular light rays from relatively large field angles do not impinge or only impinge inadequately on the retina.

In particular those light rays that enter the eye at relatively high incident angles of in particular over 60° with respect to the main viewing direction (the same as the orientation of the eye or line of symmetry of the wide-angle optical unit in the eye) are either not passed on in the eye by the optical unit or are projected on the retina within the aforementioned restricted projection range.

Using a decoupling structure such as the described annular prism, the range of vision can be divided into the two aforementioned portions, thereby accommodating the natural division of the range of view into a central foveal range of view and a peripheral range of view arranged around this. The foveal vision provides a sharp visual impression of a very limited field of vision angle about the line of symmetry of the eye lenses or the eye orientation. In this case, a range of vision of merely less than 5° (typically from 1-2°) is projected onto the fovea centralis (fixation point), the central region on the retina, i.e. the region of the sharpest vision in the human eye. Unlike this foveal vision, the peripheral vision provides blurred visual impressions outside the fixation point in the remaining angular range of the projectable field of view. In addition, owing to its structure, the human retina outside the fovea centralis up to its edge regions is very efficient in terms of object movements, is much more sensitive to light and dark by comparison with the fovea centralis, and is therefore necessary for sight in twilight and darkness. The peripheral vision is thus responsible for the provision of the primary impression of a scene as a whole, for the detection of object movements, and for vision in twilight.

In the case of human peripheral vision, the information entering the eye from the wide-angle range also has to be projected onto the peripheral regions of the retina, since the sensory cells required for peripheral vision only exist in the outer regions of the retina.

The shape and the difference in refractive indices of the decoupling structure with respect to the vitreous body causes further reflection-free deflection of the penetrating light ray, preferably into the peripheral regions of the retina.

One embodiment provides an annular prism which is mounted in a form-fitting manner onto the boundary surface and is preferably also fixed in position thereon. If the annular prism is arranged on a proximal-side shifting lens, said lens moves together with the annular prism with respect to both the preferably proximal exit window on the housing side and the transition to the vitreous body.

An alternative embodiment provides an annular prism which allows relative movements with respect to a proximal-side shifting lens (or alternatively a lens system or a lens having a variable refractive power). The annular prism is not rigidly connected to the shifting lens, but rather is preferably an integral component of for example the exit window on the housing side, yet surrounds all or part of the peripheral boundary surface of the proximal shifting lens. The shiftability between the shifting lens and the annular prism achieves a field of vision that varies with the shifting and is detectable by the retina.

Therefore, the features of the wide-angle optical unit include both various refractive optical lenses which are tailored to the specific dimensions of the implant, are made of different optical materials and have different refractive powers, and preferably a prismatic decoupling structure, which radially encloses the optical unit and can be adapted to each anatomy. It is within the scope of the invention to also use only individual segments of the decoupling structure depending, for example, on the anatomy of the patient and the demands on the optical unit of the implant.

The wearer of a complex implant equipped with a wide-angle optical unit is guaranteed a peripheral vision as provided by the natural human lens. This eliminates the aforementioned tunnel vision, which is caused by the structural restriction of the field of vision owing to the design of the implant, and allows the patient to orient themselves in space, to detect all of the scene, to react to lateral stimuli, and to see in twilight and in low light. The wide-angle optical unit is used to increase the safety and the quality of life of the implant wearer. Technical features and advantages and effects of a wide-angle optical unit according to one embodiment of the invention can be summarised as follows: combining a plurality of optical components to increase the field of vision detectable by the retina, arranging the individual optical components such that aberrations can be compensated for, providing prismatic structures, which surround the optical system at least in part, for decoupling and spreading out the rays which enter the optical system from relatively high field angles in order to ensure projection into the periphery of the retina. The decoupling structure can be adapted to the anatomy of the implant wearer.

FIG. 1 is a sectional view of an optical system comprising a wide-angle optical unit and a shifting lens for ophthalmological implants for the embodiment of an artificial accommodation system. In the embodiment shown, the refractive power of the optical system is adjusted by means of a three-lens system, comprising a lens system 2 having a high angular acceptance, and a shifting lens 3 and a trailing lens 4 having a common optical axis 5. The shifting lens, which is biconcave in the example, can be shifted relative to the lens system and the trailing lens along the optical axis. The trailing lens ensures a basic refractive power, specific to the patient, of the optical system and thus of the ophthalmological implant, allows aberrations to be compensated, and is used as a proximal exit window for the accommodation system towards the vitreous body of the eye. Together with the lens system 2, the optical system shown comprises an optical component which increases the angular acceptance of both the three-lens optical system, which is required for setting the desired accommodation state, and the decoupling structure 6, which is mounted on the boundary surface 7 around the shifting lens 3 and is used for decoupling and spreading the wide-angle ranges towards the retina.

The lens system 2 is designed to have five individual lenses 8, 9, 10, 11 and 12, which rest on one another in a planar manner and are preferably also fixed in position with respect to one another, such that the angular acceptance of the optical system as a whole is increased. For this purpose, the individual lenses are designed for example as follows. The first lens 8 is a uniconcave lens made of a glass having a refractive index of 1.716 at a wavelength of 632.8 nm (N-KZFS8 from the company Schott, Mainz), the flat lens surface acting as a distal-side emergent surface. The second lens 9 is a concave-concave lens made of the colour-correcting barium crown glass having a refractive index of 1.567 at a wavelength of 632.8 nm (N-BAK4 from the company Schott, Mainz). In the embodiment, the profiles of the first two lenses 8 and 9 rest on one another in a form-fitting manner and, when fitted together, form a compound lens which is abutted in a form-fitting manner on the proximal side by the third lens 10, a biconvex lens. The third lens 10 consists of a glass having a refractive index of 1.845 at a wavelength of 632.8 nm (N-LASF9 from the company Schott, Mainz). Together with the third lens, a biconcave fourth lens 11 made of a glass having a refractive index of 1.457 at a wavelength of 632.8 nm (Lithosil-Q from the company Schott, Mainz) also forms a compound lens, which is adjoined in a form-fitting manner at its proximal lens surface by the fifth, biconvex lens 12. The end of the lens system 2 is formed, proximally to the shifting lens, by the fifth, biconvex lens 12 made of polymethylmethacrylate having a refractive index of 1.508 at a wavelength of 632.8 nm (PMMA, acrylic-2 according to) the refractive index database of Filmetrics, Inc.

In this context, in order to increase the angular acceptance, the lens system is composed of materials having different refractive indices and adapted curvatures, in order to prevent total reflection at the material transitions. For this purpose, it has been selected in the embodiment to alternate between high and low refractive indices. The minimum number of lenses and components and the selection of the materials are dependent on the minimum requirements placed on both the lens system and the angular acceptance.

In the embodiment shown, the prismatic decoupling structure 6 is selected as a closed annular structure. The material of the decoupling structure can be tailored to the material of the housing of the ophthalmological implant. In this embodiment, PMMA has been selected as the material.

Figure 2D:
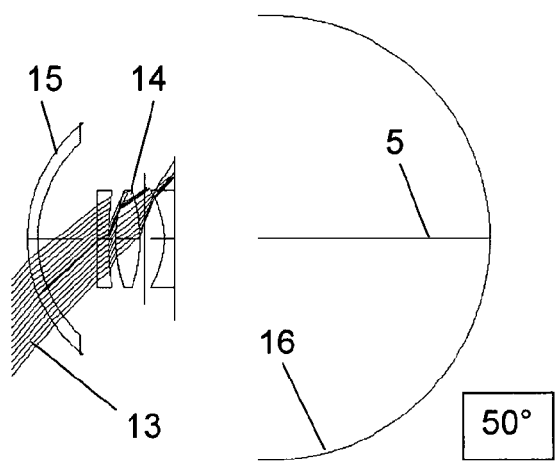
FIGS. 2a to 2r are a series of calculated light ray courses in conventional optical units (a) to (i) and wide-angle optical units (j) to (r) according to one embodiment of the artificial accommodation system in place of the natural human lens, by means of a schematic model of the human eye having an optical system with an adjustable refractive power.
Figure 2M:
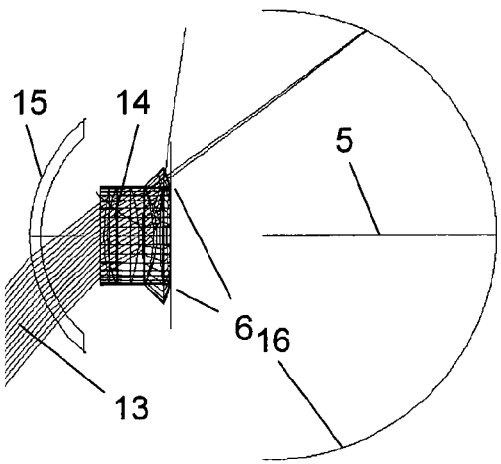
Figure 2E:
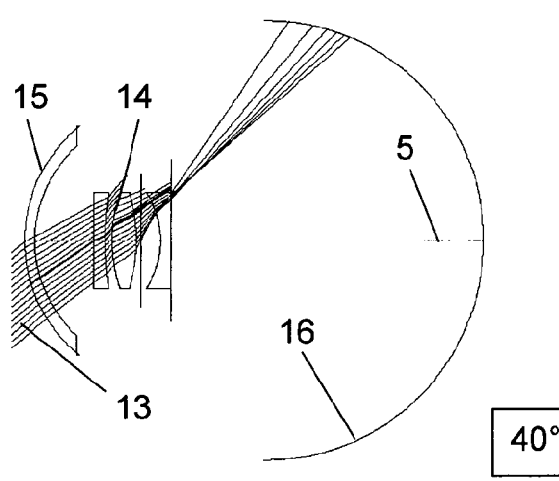
Figure 2N:
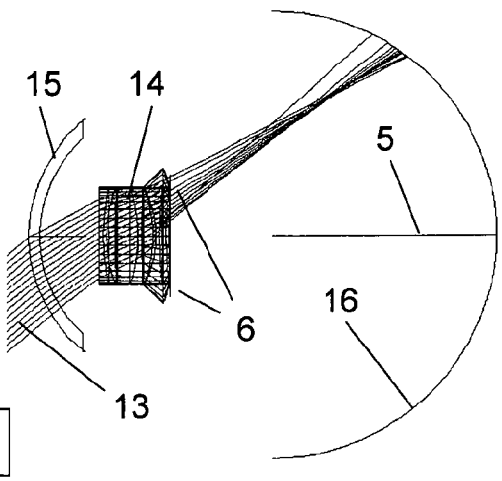
Figure 2F:
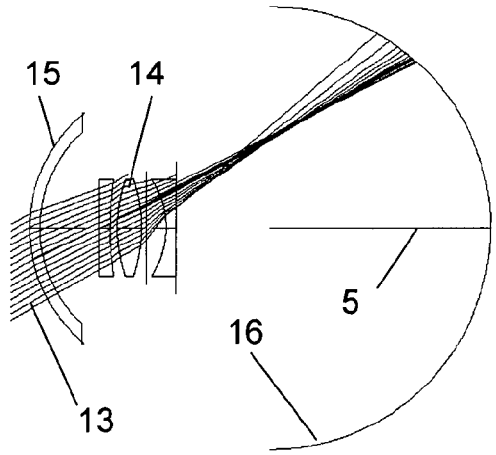
Figure 2O:
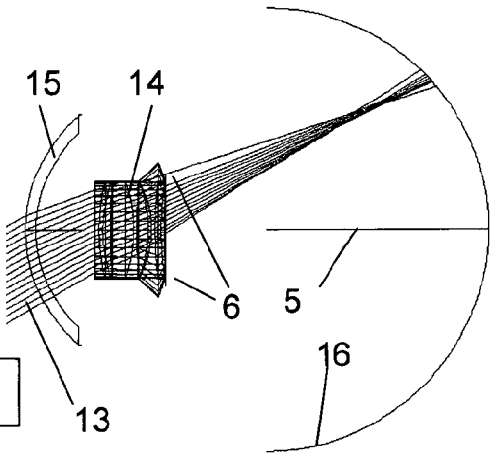
Figure 2G:
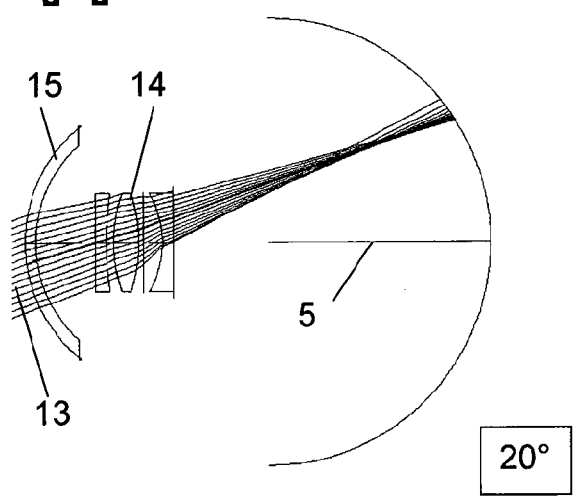
Figure 2P:
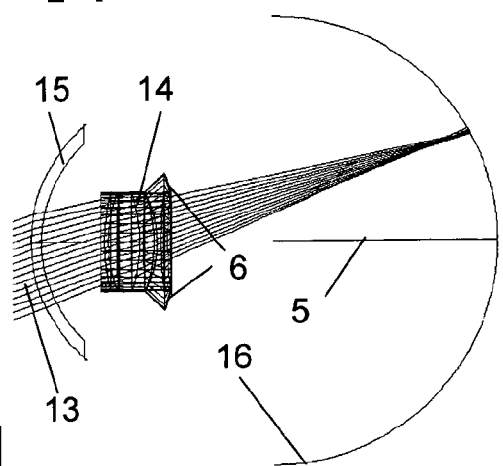
Figure 2H:
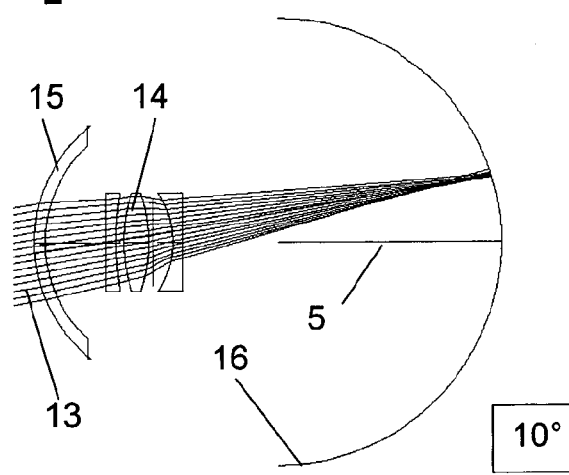
Figure 2Q:
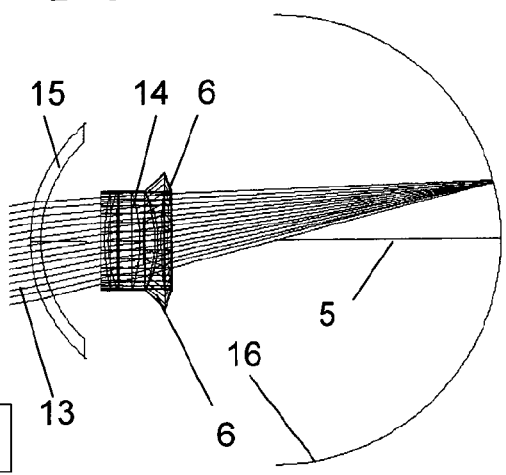
Figure 2I:
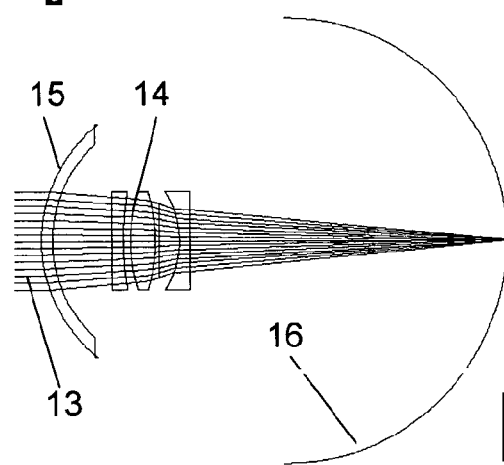
Figure 2R:
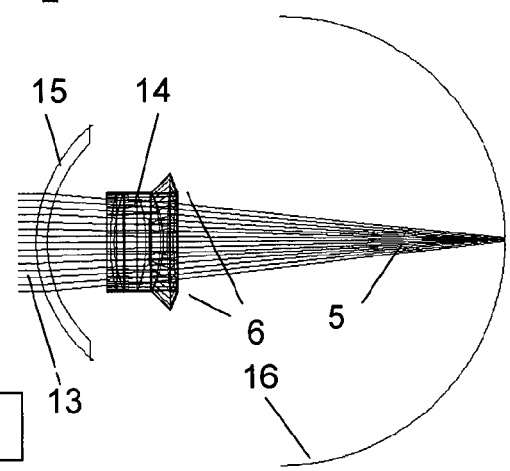

FIG. 2*a* to *r* show a series of calculated light ray courses on the basis of a schematic model of the human eye having an optical system of adjustable refractive power, in one embodiment of the artificial accommodation system, in place of a natural human lens. The on the basis of a schematic model of the human eye. The drawings schematically show the light ray course 13, the incident angle (half field angle) line-by-line, the optical axis 5, and the optical system 14 in the eye, which is shown by the cornea 15 and the retina 16 representing the eyeball. A three-lens optical unit is used in this case as a model optical unit having adjustable refractive power. The left-hand column (FIG. 2a to i) shows the results of the beam course calculations without the wide-angle optical unit and the right-hand column (FIG. 2j to r) shows the results with the wide-angle optical unit.

Calculations were made of beams of the half field angle range of from 0-85° in 10° steps up to 70° and then at 85°. The half field angle is the same as the incident angle of the light ray 13, which is incident on the cornea 15, with respect to the optical axis 5 and is indicated below each image pair, i.e. line-by-line, in FIG. 2a to r. The beam course goes from left to right. As shown in the left-hand column of drawings (without the wide-angle optical unit), it is clear from the calculated light ray courses that only beams that hit the cornea at a half field angle that is less than exactly 40° are actually passed on to the retina. Beams that hit the optical system at a greater incident angle undergo total reflection at the boundary surfaces, and more specifically, at an incident angle of 50°, at the boundary surface to the third lens, and as early as at the boundary surface of the first lens when the incident angle is even higher. This leads to what is referred to as tunnel vision, since information at incident angles of more than 40° do not reach the retina and an overall limited region on the retina is used for detection.

The right-hand column of drawings shows the same optical principle for the variation in refractive power in combination with the wide-angle optical unit. The angular acceptance, i.e. the maximum incident angle, up to which an incident light ray is passed on to the retina by the wide-angle optical unit, is increased from 40° to 85° by the wide-angle optical unit alone. In the process, a significantly larger range of the light ray is detected on the spherical retina by comparison with the left-hand column of drawings, and the wearer of the eye implant subjectively no longer perceives this as the aforementioned tunnel vision, or said wearer perceives this as tunnel vision but only to a significantly reduced degree.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

REFERENCE SYMBOL LIST 1 lens system
2 shifting lens
3 trailing lens
4 optical axis
5 decoupling structure
6 boundary surface
7 lens made of N-KZFS8
8 lens made of N-BAK4
9 lens made of N-LASF9
10 lens made of Lithosil-Q
11 Lens made of PMMA
12 light ray
13 optical system
14 cornea
15 retina

The invention claimed is:

1. A wide-angle optical unit for ophthalmological implants in an eye, comprising:
    a lens system arranged in a rotationally symmetrical manner about an optical axis;
    at least two lenses that rest one on top of the other in a planar manner and that are made of materials having different optical refractive indices,
    a trailing lens arranged proximally with respect to the interior of the eye; and
    an optical decoupling structure mounted around the trailing lens.

2. The wide-angle optical unit according to claim 1, further comprising at least one of a mechanically shiftable lens combination and a lens body having an adjustable focal length.

3. The wide-angle optical unit according to claim 2, wherein at least one of the trailing lens, the shiftable lens combination, and the lens body comprises an annular peripheral boundary surface upon which the optical decoupling structure is mounted.

4. The wide-angle optical unit according to claim 3, wherein the decoupling structure adjoins, in a form-fitting manner, all or part of the peripheral boundary surface.

5. The wide-angle optical unit according to claim 3, wherein the decoupling structure adjoins all or part of the peripheral boundary surface in at least one of a contactless manner and a relatively movable manner.

6. The wide-angle optical unit according to claim 1, wherein the decoupling structure does not have a constant structure cross section in the peripheral direction.

7. The wide-angle optical unit according to any of claim 1, wherein the decoupling structure consists of annular segments which together cover all or part of the peripheral boundary surface.

8. The wide-angle optical unit according to claim 1, characterised in that the decoupling structure is formed at least one of by at least one annular prism and by annular prism segments.

9. The wide-angle optical unit according to claim 1, wherein the trailing lens and the decoupling structure have different refractive indices.

10. The wide-angle optical unit according to claim 1, wherein the optical decoupling structure is configured to divide an image range that can be detected by the eye into a central region and a peripheral region.

11. The wide-angle optical unit according to claim 1, wherein the optical decoupling structure is configured to divide an image range that can be detected by the eye into a central foveal range of view and a peripheral range of view arranged around the central foveal range of view.

12. The wide-angle optical unit according to claim 1, wherein the trailing lens comprises an annular peripheral boundary surface; and
   wherein the optical decoupling structure is a closed annular structure that adjoins, in a form-fitting manner, the annular peripheral boundary surface.

\* \* \* \* \*